US011925816B2

(12) United States Patent
Schoengood et al.

(10) Patent No.: US 11,925,816 B2
(45) Date of Patent: Mar. 12, 2024

(54) TREATMENT OF MUCOSITIS USING PHOTOBIOMODULATION

(71) Applicant: Ronald L. Rubin, Boca Raton, FL (US)

(72) Inventors: Bradley Sean Schoengood, Manalapan, NJ (US); Ronald L. Rubin, Boca Raton, FL (US)

(73) Assignee: Ronald L. Rubin, Boca Raton, FL (US)

( * ) Notice: Subject to any disclaimer, the term of this patent is extended or adjusted under 35 U.S.C. 154(b) by 0 days.

(21) Appl. No.: 17/985,731

(22) Filed: Nov. 11, 2022

(65) Prior Publication Data

US 2023/0074559 A1 Mar. 9, 2023

Related U.S. Application Data

(63) Continuation of application No. PCT/US2021/039629, filed on Jun. 29, 2021.

(60) Provisional application No. 63/102,757, filed on Jun. 29, 2020.

(51) Int. Cl.
*A61N 5/067* (2006.01)
*A61N 5/06* (2006.01)

(52) U.S. Cl.
CPC ........... *A61N 5/067* (2021.08); *A61N 5/0613* (2013.01); *A61N 2005/0606* (2013.01); *A61N 2005/0627* (2013.01)

(58) Field of Classification Search
CPC .............. A61N 5/067; A61N 5/0613; A61N 2005/0606; A61N 2005/0627; A61N 2005/0644; A61N 2005/0659; A61N 5/0603
See application file for complete search history.

(56) References Cited

U.S. PATENT DOCUMENTS

| 4,905,690 A * | 3/1990 | Ohshiro | A61N 5/0616 607/89 |
| 2002/0120312 A1 * | 8/2002 | Ignatius | A61N 5/0616 607/90 |

(Continued)

FOREIGN PATENT DOCUMENTS

WO 2022006117 1/2022

OTHER PUBLICATIONS

International Search Report and Written Opinion for International Application No. PCT/US21/39626 from the International Searching Authority at the United States Patent and Trademark Office, Authorized by Officer Kari Rodriguez, dated Oct. 13, 2021.

(Continued)

*Primary Examiner* — Yingchuan Zhang
*Assistant Examiner* — Sebastian X Lukjan
(74) *Attorney, Agent, or Firm* — The Concept Law Group, PA; Scott D. Smiley; Scott M. Garrett

(57) ABSTRACT

A method for treating an oral cavity malady of a patient, comprising: applying a spot of a laser beam to a target area around the oral cavity, said laser beam having a wavelength of about 800 to 840 nm and a power of between 1000 and 4000 mW, and wherein said spot has a spot size of about 1 to about 10 mm; and moving said spot on said target area for a treatment time sufficient to deliver a dose of about 0.5 to about 30 J/cm² to said target area.

1 Claim, 2 Drawing Sheets

(56) References Cited

U.S. PATENT DOCUMENTS

| | | | | |
|---|---|---|---|---|
| 2008/0058908 A1* | 3/2008 | Bornstein | ............ | A61C 19/063 |
| | | | | 607/93 |
| 2009/0054953 A1* | 2/2009 | Whitehurst | .......... | A61N 5/0616 |
| | | | | 607/88 |
| 2015/0112411 A1* | 4/2015 | Beckman | ............. | A61N 5/0616 |
| | | | | 607/90 |
| 2016/0166848 A1* | 6/2016 | Bouboulis | ............ | A61N 5/0603 |
| | | | | 607/92 |
| 2016/0279436 A1* | 9/2016 | Wang | ....................... | A61N 5/06 |
| 2019/0254775 A1* | 8/2019 | Gregg, II | ................ | A61C 19/06 |

OTHER PUBLICATIONS

Freitas et al., "Proposed Mechanisms of Photobiomodulation or Low-Level Light Therapy." IEEE Journal of Selected Topics in Quantum Electronics vol. 22. No. 3 (May/Jun. 2016), pp. 1-17.

* cited by examiner

TREATMENT OF MUCOSITIS USING PHOTOBIOMODULATION

REFERENCE TO RELATED APPLICATIONS

This application claims priority to PCT Application No. PCT/US2021/039629, filed Jun. 29, 2021, and claiming priority to U.S. Provisional Application No. 63/102,757, filed Jun. 29, 2020, each of which are hereby incorporated by reference in their entireties.

FIELD OF INVENTION

The invention relates generally to the treatment of mucositis, and, more specifically, to the treatment of mucositis using a focused laser beam.

BACKGROUND

Mucositis is a complication of cytotoxic cancer treatments, such as chemotherapy and radiation. As a result of such highly toxic cancer treatments, the rapidly dividing epithelial cells of the gastro-intestinal cells can break down. This leaves the mucosal lining susceptible to many classes of damage, for instance ulceration and infection. Of note, the mucosa virtually lines every organ in the body from the gastrointestinal tract to the pulmonary tree. This point is important given that we are presenting a novel treatment that has the potential to treat any mucosal lining affected by cancer treatment.

Of all areas that can be affected by Cytotoxic treatment, the oral cavity including the cheeks, lips, gums, inner cavity, and tonsillar region—all of the soft tissues are the most common locations for mucositis. Oral Mucositis is likely the most common, debilitating complication of cancer treatments, especially chemotherapy and radiation. Symptoms and sequelae typical of oral mucositis include red, shiny, or swollen mouth and gums, blood in the mouth, sores in the mouth or on the gums or tongue, soreness or pain in the mouth or throat, difficulty swallowing or talking, and xerostomia, mild burning, or pain when eating food. Furthermore, soft, whitish patches or pus in the mouth or on the tongue are frequently seen in addition to increased mucus or thickened saliva in the mouth. In some cases, oral mucositis presents in an extreme form called confluent mucositis, in which case the mucous membrane of the patient's entire mouth and tongue can be coated by a white mucus coating that is up to a millimeter thick, making it nearly impossible for the patient to eat food. It has a significant effect on the patient's quality of life and can be dose-limiting with respect to the cancer treatment, a highly undesirable consequence of mucositis when the cancer team is trying to adequately treat a malignancy.

Treatment options today are limited once mucositis sets in. Patients are usually given pain medication and/or antiseptic mouthwash. Beyond that, there is not much doctors can do for the painful condition that, at advanced stages, can inhibit a patient's ability to eat and speak.

More recently, the use of photobiomodulation (PBM) has been introduced to treat mucositis. PBM is a light therapy in which laser light or light emitting diode (LED) light is applied to tissue to improve tissue repair, reduce pain and inflammation. PBM (also termed low laser light therapy (LLLT) functions according to first law in photochemistry [Grotthuss-Draper law]. According to this law, light must be absorbed by a chemical substance in order to generate photochemical reaction. In PBM, that chemical substance is represented by the respiratory enzyme Cytochrome C oxidase, which is involved in the electron transport chain that occurs in the mitochondria of cells. Mitochondria are the "powerhouse" of the cell, the subcellular organelle in which the TCA cycle takes place, allowing an oxygen molecule to be converted into 46 ATP (adenosine triphosphate), the form of energy that is usable by the human body. It is believed that low-level radiation is absorbed by intracellular photoreceptors in the membrane of the mitochondria. The effects include a reduction in pain due to increased endorphins, reduction in inflammation via reduction in interleukin-1 and C-reactive protein and tissue healing effects as a result of increased neovascularization and macrophage activity.

While PBM therapy is promising, Applicant recognizes shortcomings in current approaches. For example, current approaches tend to use bulky, desktop units, which emit a diffused beam and require contact with the tissue being treated. Such contact can cause irritation (e.g., on ulcers and other open sores) and raises sterilization concerns. Accordingly, Applicant identifies the need for a maneuverable, handheld device, which need not contact with the tissue being treated. The present invention fulfills this need, among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicant recognizes that by administering PBM therapy using a relatively high-powered spot of far red to near infrared (NIR) laser light, rather than diffused light, the effectiveness of the PBM therapy is enhanced significantly. More specifically, Applicant has developed an approach/device which emits a laser light having a precisely controlled spot size. The small spot size compared to a diffused light intensifies the dose of light at the target, thereby eliminating the need to contact the tissue with the device. Indeed, often the oral cavity can be treated without inserting the device in the mouth if the laser spot can be directed at the target area from outside the mouth. Additionally, the high-energy laser spot reaches deep into the tissue to create a more powerful therapeutic anti-inflammatory, anti-edema and analgesic effect speeding up the healing process at the same time. Furthermore, Applicant has discovered that the small laser spot size in combination with the far-red to NIR light (e.g. 800-840 nm) is particularly effective at stimulating mitochondria. For example, in one embodiment, a 1-2 minute exposure per 10 $cm^2$ of target area was found to be sufficient to initiate mitochondrial stimulation.

Moreover, in one embodiment, the device is handheld and maneuverable, therefore allowing the user to control the spot size on the target area for a given duration with a high degree of control and precision. This is particularly beneficial given the relatively high energy of the laser spot and the need to control it carefully.

Therefore, using the approach of the present invention, the device is able to transfer laser energy more efficiently to the anatomical structures to which the therapy is directed in comparison with traditional laser emissions. By having full control of the precise spot size, the emissions, the distribution of energy into the tissues becomes more homogenous, in contrast to older generation lasers. This, in part, explains the increased efficacy and longer-term outcomes seen with the approach of the present invention. The result is a hand-held portable laser technology which has an optically sophisticated precise and adjustable spot-size laser beam that works on a specific area throughout the oral cavity, including the oropharynx, to (a) reduce intensity and duration of pain; (b) shorten healing and rehabilitation period; and (c) increase quality of life and peace of mind with regards patient's recuperation.

In one embodiment, the present invention relates to a method for treating an oral cavity malady of a patient, comprising: (a) applying a spot of a laser beam to a target area around the oral cavity, the laser beam having a wavelength of about 800 to 840 nm and a power of between 1000 and 4000 mW, and wherein the spot has a spot size of about 3 mm to about 3.5 mm; and (b) moving the spot on the target area for a treatment time sufficient to deliver a dose of about 0.5 to about 30 $J/cm^2$ to the target area.

In one embodiment, the present invention relates to a device for treating an oral cavity malady of a patient, comprising: (a) a hand-held housing; (b) at least one laser disposed in the housing and configured for emitting a laser beam have a peak wavelength of 800-840 nm, and a power of 1000-4000 mW; (c) at least one battery for powering the laser; (d) a display screen for displaying at least a duration of time the laser is operating; (e) operator controls for at least starting and stopping the laser.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

In one embodiment, the present invention relates to a method for treating an oral cavity malady of a patient, comprising: (a) applying a spot of a laser beam to a target area around the oral cavity, the laser beam having a wavelength of about 800 to 840 nm and a power of between 1000 and 4000 mW, and wherein the spot has a spot size of about 2 mm to about 10 mm; and (b) moving the spot on the target area for a treatment time sufficient to deliver a dose of about 0.5 to about 30 $J/cm^2$ to the target area.

Figure 1:
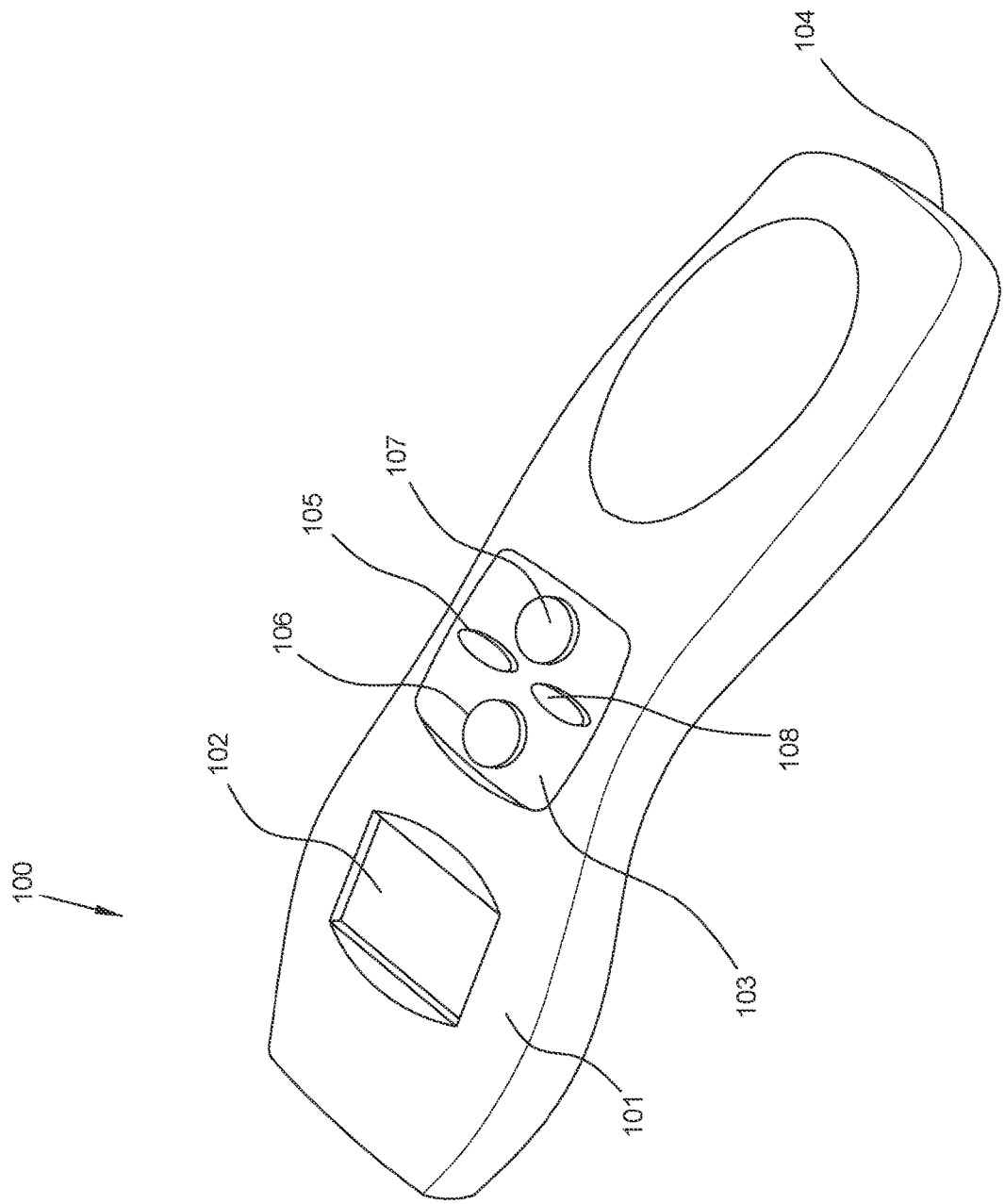
FIG. 1 shows the top view of one embodiment of the device of the present invention.
Figure 2:
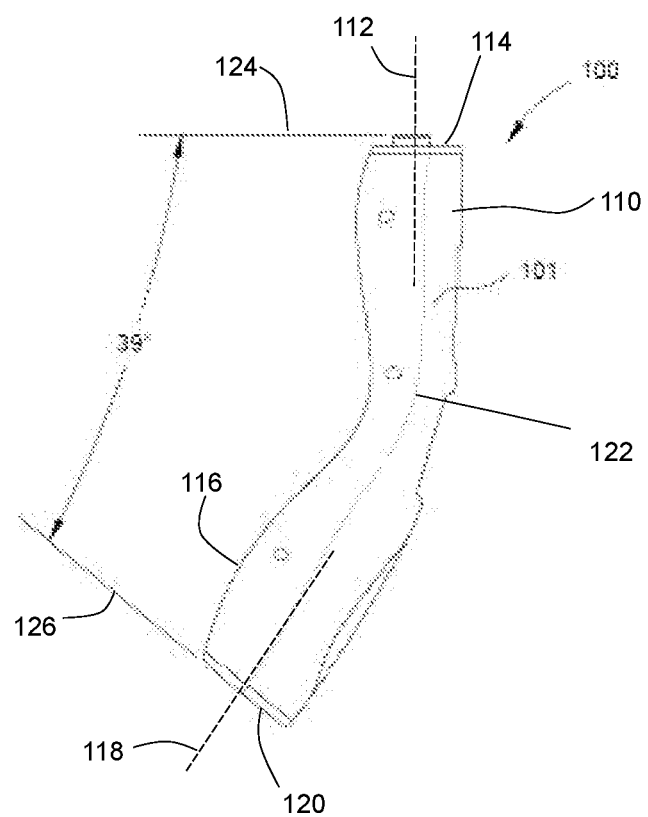
FIG. 2 shows a side view of the embodiment of FIG. 1.

Referring to FIGS. 1 and 2, one embodiment of a device 100 of the present invention for treating mucositis using photobiomodulation it is shown. The device comprises: a hand-held housing 101; at least one laser (not shown) disposed in the housing and configured for emitting a laser beam have a peak wavelength of 800-840 nm, and a power of 1000-4000 mW; at least one battery (not shown) disposed in the housing for powering the laser; a display screen 102 for displaying an indication of at least a treatment time; and operator control 103 for at least starting and stopping the laser.

Each of these features is described below in greater detail and with reference to selected alternative embodiments.

As used herein, the term "oral cavity" refers to the mouth and upper part of the throat, and includes, the lips, the lining inside the cheeks and lips, the tongue, the upper and lower gums, the floor of the mouth under the tongue, the bony roof of the mouth, area behind the wisdom teeth, and the upper part of throat; and the term "oral cavity malady" refers to any pain, wound, infection, infestation, etc. of the oral cavity, and includes, for example, mucositis, gingivitis, stomatitis, cankers, sores, ulcers, muscular tension problems resulting from procedures that cause inflammation (extractions, root canal work, dental implants, interventions on soft tissue, etc.), post-surgery pain after interventions for inserting dental implants; healing is also promoted (and as a result less analgesics need to be taken), muscle tension preventing bite registration, and trigeminal neuralgia, just to name a few.

One aspect of the invention is Applicant's discovery of an effective wavelength for the laser beam for stimulating the mitochondria to treat mucositis. In one embodiment, the laser beam has a wavelength of about 800-840 nm, or, in another embodiment, about 810-830 nm, or, in another embodiment, about 810 or about 830 nm.

Another aspect of the invention is Applicant's discovery of an effective power for the laser beam for stimulating the mitochondria to treat mucositis. In one embodiment, the laser is a continuous beam laser. In one embodiment, the laser beam has a power of 1000 mW to 4000 mW, or, in another embodiment, a power of 1500 mW to 3000 mW, or, in another embodiment, a power of about 2000 mW. In one embodiment, the power is no greater than about 2000 mW to reduce the potential for pain, bleeding, ablation, and damage to tissues.

The dose of laser light for stimulating the mitochondria is a function of several factors including energy of beam, spot size, treatment area and treatment time. In one embodiment, the dose is about 0.5 to about 30 $J/cm^2$, or, in one embodiment, about 5 to about $J/cm^2$, or, in one embodiment, about 10 to about 24 $J/cm^2$, or, in one embodiment, about 2 to about 10 $J/cm^2$, or, in one embodiment, about 2 to about 4 $J/cm^2$. Those of skill in the art will understand that, in light of this disclosure, the dose of light is determined based upon a number of variables including thickness of the tissue being treated.

Yet another aspect of the invention is Applicant's control over the dose by varying spot size. The dose is inversely proportional to the spot size. In one embodiment, the spot size is about 1 mm to about 10 mm, or, in one embodiment, about 2 mm to 6 mm, or, in one embodiment, about 3 mm to 4 mm.

As mentioned above, because of the maneuverability of the hand-piece, in one embodiment, the spot size of the laser can be controlled by varying the distance between the device and the target area. For example, in one embodiment, varying the distance from about 2 cm to 5 cm results in a spot size change of about 1 mm to about 4 mm. Alternatively, in one embodiment, rather than (or in addition to) adjusting the distance between the device and the target area, the spot size is controlled by adjusting an optical component (e.g., lens, or focal distance) of the device emitting the laser beam.

In one embodiment, the treatment time (T) for each application is calculated by T (sec)=D ($J/cm^2$)×A ($cm^2$)/P (W), where D is dose, A is treatment area, and P is power. For example, if the dose is 12 J/cm², power is 2 W, and a treatment area is 10 cm², then the treatment time is 60 seconds.

Because of the relatively high power of the laser spot, it is important to keep the laser spot moving continuously, and avoiding holding it in one location for too long. For example, suitable results have been obtained by holding the laser beam spot in the same location for no longer than 5 seconds, or for no longer than three seconds. Those of skill in the art will be able to determine, without undue experimentation, the proper rate at which to move the laser spot in light of this disclosure. Generally, although not necessarily, the laser spot is applied to tissue by moving the laser spot is a circular motion in the treatment area.

In one embodiment, the device is configured to alert the user that the laser spot has been focused on the same location for too long. For example, in one embodiment, the device comprises one or more accelerometers to ensure that the device is always moving when the laser beam is being emitted, and to alert the user to modify the rate at which the laser spot is being moved to ensure optimal results.

In one embodiment, the device comprises a timer to ensure that the user delivers the laser energy for the appropriate treatment time. In other words, once the appropriate treatment time is determined (as described, for example, above), this time can be entered by the user into the device. The device then monitors the time that the laser is emitting, and either stops emitting the laser beam once the treatment time is reached, or alerts the user that treatment time has expired. In one embodiment, if the user stops the laser beam before treatment time is expired, the timer pauses until the user starts the laser again.

The treatment area may be extraoral or intraoral. In one embodiment, the laser does not necessarily go into the mouth unless the patient develops a lesion inside the mouth that needs to be targeted. Instead, in one embodiment, treatment is performed in various sites (e.g., five) along a patient's face and along the jaw line. In one embodiment, the procedure also involves treating a patient's tongue. Even if the treatment is intraoral, there is typically no need to insert the device in the patient's mouth. Rather, if there is line-of-sight between the opening of the patient's mouth and the target area, the laser beam can be applied from outside the patient's mouth. It is generally preferred for the patient to wear glasses configured to block or reflect a significant portion of light at about 800 to 840 nm during the procedure.

As discussed above, the mechanism by which the laser affects cells is understood to be based on bio-stimulation. It is believed that low level radiation is absorbed by intracellular photoreceptors in the membrane of the mitochondria. The effects include a reduction in pain due to increased endorphins, reduction in inflammation via reduction in interleukin-I and C-reactive protein and tissue healing effects as a result of increased neovascularization and macrophage activity. In one embodiment, the treatment time is sufficient to increase neutrophil count to above 1000 cell/nm³, or, in one embodiment, above 1200 cell/nm³.

The method and device of present invention may be used to treat a variety of different oral cavity maladies including mucositis, gingivitis, stomatitis, cankers, sores, ulcers, muscular tension problems resulting from procedures that cause inflammation (extractions, root canal work, dental implants, interventions on soft tissue, etc.), post-surgery pain after interventions for inserting dental implants; healing is also promoted (and as a result less analgesics need to be taken), muscle tension preventing bite registration, and trigeminal neuralgia. Additionally, the device and method of the present invention can be used for preoperative treatments as well.

Referring to FIGS. 1 and 2, one embodiment of the device 100 of the present invention is shown. It should be understood that this embodiment is just one embodiment, and the device may take on different forms. In one embodiment, the housing 101 of the device 100 is angled. That is, the housing 101 of the device has a control portion 110 and a handle portion 116 that are contiguous from a front end 114 to a rear end 120 of the device 100, and the control portion 110 and handle portion 116 are each generally linear, but aligned on axes that that are at an angel with respect to each other. The control portion extends from the front end 114 to a midpoint 122 generally along a first axis 112, and the handle portion extends from the midpoint 122 to the rear end 120 along a second axis 118. Lines 124, 126 that are perpendicular to axes 112, 118, respectively are at an angle relative to each other. Although the angle in FIG. 2 is shown to be 39°, the device may be configured with other angles including, for example, from about 10° to about 60°, or from 20° to about 50°, or from 30° to about 40°.

In one embodiment, a power supply supplies power from batteries (e.g., rechargeable batteries) located in the housing to one or more laser diodes, and a microcontroller (not shown) provides timing functionality. As a safety feature, a removable cap may be used to prevent accidental laser emission.

In one embodiment, depressing a tail switch 104 powers on the unit when operating by battery power. When the switch 104 is pressed, the display 102 illuminates. Display 102 displays treatment information to the user. In one embodiment, an embedded software program controls the timing of the treatment as below above. The unit is powered down by pressing the power button.

In one embodiment, the device is operated in either of two modes: (1) a timer mode where treatment time is entered, and the device automatically shuts off when the set time is reached; and (2) a manual mode where treatment continues until the device is manually shut off By utilizing the manual mode, the practitioner may continue the treatment until he/she sees evidence of treatment success.

In one embodiment, to operate in timer mode, In one embodiment, depressing a tail switch 104 powers on the unit when operating by battery power. When the switch 104 is pressed, the display 102 illuminates. Display 102 displays treatment information to the user. In one embodiment, an embedded software program controls the timing of the treatment as below above. The unit is powered down by pressing the power button.

In one embodiment, to operate in timer mode, the user presses timer button 105, which puts the device in timer mode, and then sets the time by pressing the up button 107 to toggle through time increments (e.g., 15 seconds, 30 seconds, etc.). The treatment time is displayed on display 102. Pressing the start/stop button 106 causes the device to power the laser. In one embodiment, the laser emits in CW mode. Pressing the start/pause button again causing the device to stop/pause the laser, and, in one embodiment, the timer also stops/pauses. When the start button is pressed again, the timer will start from where it left off Pressing timer button 105 resets the time to 00:00.

In one embodiment, to operate in manual mode, a user presses the CW button 108, which puts the device in manual or CW mode. Next the user presses start button 106 to use the laser in continuous wave mode. Repeatedly pressing the start button 106 will cause the laser to toggle on and off.

In the foregoing specification, the disclosure has been described with reference to specific embodiments thereof. It will, however, be evident that various modifications and changes may be made thereto without departing from the broader spirit and scope of the disclosure. For example, the above-described process steps are described with reference to a particular ordering of process actions. However, the ordering of many of the described process actions may be changed without affecting the scope or operation of the disclosure. The specification and drawings are, accordingly, to be regarded in an illustrative sense rather than in a restrictive sense.

What is claimed is:

1. A method for treating an oral cavity malady in an oral cavity of a patient, the method comprising:
   providing a device that is configured to be hand-held during use, the device being battery powered and including a laser;
   applying a spot of a laser beam generated by the laser of the device to a target area in the oral cavity to stimulate mitochondria at the target area without inserting the device into the oral cavity, said laser beam having a continuous wavelength in a range from 800 nanometers (nm) to 840 nm and a power of between 1000 milliwatts (mW) and 4000 mW, and wherein said spot has a spot size of 1 millimeter (mm) to 10 mm; and
   moving said spot on said target area for a treatment time sufficient to deliver a dose of 0.5 Joules/centimeter$^2$ (J/cm$^2$) to 30 J/cm$^2$ to said target area.

* * * * *